US012788531B2

(12) United States Patent
Beyl

(10) Patent No.: US 12,788,531 B2
(45) Date of Patent: Nov. 10, 2026

(54) CALIBRATION METHOD FOR THE AUTOMATED CALIBRATION OF A CAMERA WITH RESPECT TO A MEDICAL ROBOT, AND SURGICAL ASSISTANCE SYSTEM

(71) Applicant: B. Braun New Ventures GmbH, Freiburg im Breisgau (DE)

(72) Inventor: Tim Beyl, Baden-Baden (DE)

(73) Assignee: B. Braun New Ventures GmbH, Freiburg im Breisgau (DE)

( * ) Notice: Subject to any disclaimer, the term of this patent is extended or adjusted under 35 U.S.C. 154(b) by 267 days.

(21) Appl. No.: 18/700,849

(22) PCT Filed: Oct. 12, 2022

(86) PCT No.: PCT/EP2022/078423
§ 371 (c)(1),
(2) Date: Apr. 12, 2024

(87) PCT Pub. No.: WO2023/062091
PCT Pub. Date: Apr. 20, 2023

(65) Prior Publication Data
US 2024/0407883 A1 Dec. 12, 2024

(30) Foreign Application Priority Data
Oct. 13, 2021 (DE) ..................... 10 2021 126 484.7

(51) Int. Cl.
*A61B 90/00* (2016.01)
*A61B 34/20* (2016.01)
(Continued)

(52) U.S. Cl.
CPC ............ *A61B 90/361* (2016.02); *A61B 34/32* (2016.02); *G06T 7/80* (2017.01);
(Continued)

(58) Field of Classification Search
CPC .... A61B 2034/2065; A61B 2560/0233; A61B 34/32; A61B 90/361; B25J 9/1692;
(Continued)

(56) References Cited

U.S. PATENT DOCUMENTS 9,542,743 B2 * 1/2017 Tenney .................. H04N 7/181
2017/0333137 A1 * 11/2017 Roessler ................ A61B 34/20
(Continued)

FOREIGN PATENT DOCUMENTS

WO 2020264489 A1 12/2020
WO 2021087433 A1 5/2021

OTHER PUBLICATIONS

Zhuang, Hanqi, Zvi S. Roth, and Raghavan Sudhakar. "Simultaneous robot/world and tool/flange calibration by solving homogeneous transformation equations of the form AX=YB." IEEE Transactions on Robotics and Automation 10.4 (1994): 549-554. (Year: 1994).*

(Continued)

*Primary Examiner* — Chineyere Wills-Burns
*Assistant Examiner* — Emmanuel Silva-Avina
(74) *Attorney, Agent, or Firm* — Christopher A. Rothe; CM Law

(57) ABSTRACT

A method is used for calibrating a robot camera and external camera system relative to a medical robot. The robot camera is guided on an arm. The camera system has an external camera. The method includes: moving the robot camera via the robot arm during sensing and capturing; detecting a pose of a calibration pattern and/or an external tracker, each having a transformation to a pose of the external camera, and/or detecting a pose of the external camera; determining a transformation between the robot camera and external camera, and determining a field of view; moving a flange into at least three poses in the field of view and sensing the
(Continued)

at least three poses via the external camera, and simultaneously sensing a transformation between the robot base and the flange; and performing a hand-eye calibration. The method can be used with a surgical assistance system and computer-readable storage medium.

15 Claims, 3 Drawing Sheets

(51) Int. Cl.
*A61B 34/32* (2016.01)
*G06T 7/80* (2017.01)

(52) U.S. Cl.
CPC . *A61B 2034/2065* (2016.02); *A61B 2090/397* (2016.02); *A61B 2560/0233* (2013.01); *G06T 2207/30204* (2013.01); *G06T 2207/30244* (2013.01)

(58) Field of Classification Search
CPC ........... G05B 2219/39008; G05B 2219/39045; G05B 2219/39057; G06T 2207/30244; G06T 7/80; G06T 2207/30204
USPC .......................................................... 382/103
See application file for complete search history.

(56) References Cited

U.S. PATENT DOCUMENTS

| | | | | |
|---|---|---|---|---|
| 2018/0071042 | A1 | 3/2018 | Franjic et al. | |
| 2020/0198145 | A1* | 6/2020 | Hsu ........................ | B25J 9/1697 |
| 2022/0383547 | A1* | 12/2022 | Ulrich .................... | B25J 9/1692 |
| 2022/0401178 | A1* | 12/2022 | Polchin .................. | A61B 34/20 |

OTHER PUBLICATIONS

Özgüner, Orhan, et al. “Camera-robot calibration for the da vinci robotic surgery system.” IEEE Transactions on Automation Science and Engineering 17.4 (2020): 2154-2161. (Year: 2020).*

Oezguener et al., “Camera-Robot Calibration for the Da Vinci Robotic Surgery System,” IEEE Transactions on Automation Science and Engineering vol. 17, No. 4, Oct. 2020, 8 pages.

Search Report received in German Application No. 10 2021 126 484.7 dated Jun. 13, 2022, with translation, 7 pages.

Search Report received in International Application No. PCT/EP2022/078423 dated Feb. 1, 2023, with translation, 5 pages.

Written Opinion received in International Application No. PCT/EP2022/078423 dated Feb. 1, 2023, with translation, 22 pages.

* cited by examiner

CALIBRATION METHOD FOR THE AUTOMATED CALIBRATION OF A CAMERA WITH RESPECT TO A MEDICAL ROBOT, AND SURGICAL ASSISTANCE SYSTEM

CROSS-REFERENCE TO RELATED APPLICATIONS

This application is the United States national stage entry of International Application No. PCT/EP2022/078423, filed on Oct. 12, 2022, and claims priority to German Application No. 10 2021 126 484.7, filed on Oct. 13, 2021. The contents of International Application No. PCT/EP2022/078423 and German Application No. 10 2021 126 484.7 are incorporated by reference herein in their entireties.

FIELD

The present disclosure relates to a calibration method for the automated calibration of a robot camera to and/or in relation to a medical robot, more particularly a surgical robot, and for the automated calibration of an external camera system with at least one external camera to the robot. The robot camera is movably guided in relation to a robot base on a robot arm of the robot which is connected to the robot base. In addition, the present disclosure relates to a surgical navigated assistance system/a navigated robotic manipulator, and to a computer-readable storage medium.

BACKGROUND

A typical problem in the field of medical robotics, more particularly surgical robotics, is the so-called hand-eye calibration in which a transformation between a camera and a robot is searched so as to quasi synchronise and correlate the world of sensing and/or view and the world of robot kinematics.

This hand-eye calibration comprises typically two cases or scenarios, wherein in a first case a camera is directly held and guided by the robot, a so-called eye-in-hand configuration, and in a second case an (external) camera is arranged externally, more particularly statically, and tracks the movable robot itself or a tracker/a marker which is held by the robot (so-called eye-on-basis configuration).

The purpose of this calibration is, as indicated before, to combine or to link the camera's capturing/imaging processing with the robot kinematics, so that, for instance, objects in the field of view of the camera can be identified in particular by means of image processing and/or image analysis and a plan can be established for the robot for seizing and/or manipulating these objects. Specifically, during a medical intervention the robot may carry out a manipulation of a patient's tissue by means of an end effector and a capturing provided by the camera. In addition, there are further medical scenarios which require a hand-eye calibration.

As a rule, another calibration is necessary in addition to the hand-eye calibration, namely, a so-called geometric calibration of the camera itself so as to determine optical parameters such as, for instance, the focal length of the camera. This geometric calibration is necessary to generate geometrically correct representations of the observed scene with a camera used, and to ensure precise manipulation by the robot. A calibration pattern is as a rule required for the geometric camera calibration. The calibration pattern must be placed in the field of view of the camera, and the calibration takes place with the aid of the known geometry of the pattern and a calibration algorithm which calculates camera parameters such as focal length or distortion coefficients from the observed capturings and distortions. The calibration pattern has to be moved relative to the camera, either by displacing the calibration pattern itself or by moving the camera.

Specifically, both calibrations are necessary for using a medical robot together with a camera, be it arranged externally to the robot (hand-on-base) or on the robot itself (robot camera), particularly in the area of an end effector.

Although methods for a hand-eye calibration and a geometric calibration exist in the state of the art, they have to be carried out manually in accordance with a calibration scheme by a user and are very complex. Moreover, due to the manual handling these methods are error-prone and often do not offer the necessary precision of calibration, in particular if a medical robot is to be used in a surgical intervention with tolerances of few millimetres and calibration has to be carried out prior to the intervention itself.

SUMMARY

The objects and aims of the present disclosure therefore are to avoid or at least mitigate the disadvantages from the state of the art, and more particularly to provide a calibration method, a surgical assistance system/a navigated robotic manipulator, and a computer-readable storage medium which provides in an automated manner, i.e., without necessary manual input by a user, in a particularly simple, quick, efficient, and accurate manner, a calibration/registration/correlation between a robot and a camera. A further partial object consists in carrying out such calibration with as few medical devices as possible and especially with standardised medical devices so as not to be obliged to hold additional devices available in an operating theatre apart from the devices used during the operation, and to keep the costs low. A further partial object is to provide an intuitive and automated calibration for the user, more particularly the surgeon, so that the user, more particularly medical professionals, does/do not require a particular calibration training.

The objects are solved with respect to a generic calibration method/registration method, with respect to a generic surgical assistance system, and with respect to a computer-readable storage medium.

Thus, an automated calibration method/registration method and an automated/automatic calibration system are provided which carry out a calibration between a camera mounted on a robot (robot camera) and an (external) camera system observing the robot. In the present configuration, in contrast to the state of the art, at least two cameras are used, wherein an external camera is mounted on a base (eye-on-base) and a further camera (robot camera) is mounted on the robot (eye-in-hand) so as to be controlled and moved actively. The process of calibration may be carried out in an automated manner, more particularly sequentially, by means of the automated calibration method. The present disclosure enables to calibrate and/or register both cameras, i.e., both the external camera and the robot camera, together with the robot. Thus, both cameras are calibrated to the robot. Due to the automated calibration with involved redundancy it is also possible to minimize an error, for instance, if medical professionals move into the field of view of between the external camera and the robot and obstruct the view. In this case, the calibrated robot camera may possibly continue the control.

A basic idea of the present disclosure thus consists in providing a camera both on the robot itself (eye-in-hand) which is movable by means of the robot arm, and additionally an external camera (eye-on-base) which senses the robot arm or an end portion of the robot arm for tracking and senses at least a robot flange and/or a tracker when it moves into the field of view of the external camera. In a first step of the automated calibration the robot camera (eye-in-hand) is moved such that it senses the external camera (eye-on-base) and determines a suitable transformation between the robot camera (eye-in-hand) and the external camera (eye-on-base). In a further step the robot flange, more particularly a tracker/marking element mounted on the robot flange, is then moved in the field of view of the external camera, and the robot flange, more particularly the tracker, is tracked (with respect to a pose). The kinematics of the robot between the robot base and the robot flange may be sensed by means of the control and also a transformation between the robot base and the robot base may be provided by means thereof. On this basis, the hand-eye calibration is finally carried out. With the present disclosure a simultaneous calibration/registration between the robot camera and the robot as well as the external camera and the robot is carried out.

This configuration is especially important in a surgical scenario in which the external camera (eye-on-base) is, for instance, a tracking camera which is used for tracking the robot used as a tool in a surgical navigation scenario. Just as important is, of course, also the case in which an optical camera is used for an optical capturing. The camera held by the robot (robot camera; eye-in-hand) may likewise especially be a tracking camera for tracking or an optical camera.

In the field of medicine the robot camera held by the robot may, for instance, be used to obtain a more detailed image of the patient (in particular for image processing). Alternatively or additionally, the camera could also be a microscope camera, wherein the robot and camera assemblies form a surgical microscope. In another medical scenario the robot camera may, for instance, be used for the visualisation of objects which are not visible by the camera on the base.

In other words, a calibration method for the automated calibration of a robot camera to a robot, which is movably guided on a robot arm with a robot flange of the robot, which is connected to a robot base, and for the automated calibration of an external camera system with at least one external camera to the robot, comprises the steps of: moving the robot camera (eye-in-hand) by means of the robot arm during sensing and capturing an environment; detecting a predefined optical calibration pattern and its pose with predefined transformation/relation to a pose of the external camera and/or detecting a pose of the external camera on the basis of the capturing; determining, on the basis of the ascertained pose of the external camera, a transformation between the robot camera and the external camera and determining a field of view of the external camera; moving the robot flange, more particularly with at least one tracker/marking unit mounted on the robot flange, into at least three different poses in the (previously defined) field of view of the external camera and sensing the at least three poses of the robot flange, more particularly the poses of the tracker, by means of the external camera and simultaneously sensing a transformation between the robot base and the robot flange; and carrying out, on the basis of the at least three sensed poses and the at least three transformations, a hand-eye calibration with determination of a transformation from the robot flange to the robot camera (eye-in-hand) and to the external camera (eye-on-base).

The expression "calibration pattern" defines a pattern used in this field of image analysis. Specifically, standardised calibration patterns are used, such as, for instance, a QR code or a chequered black-and-white pattern with additional markings.

The expression "position" means a geometric position in the three-dimensional space which is indicated in particular by means of coordinates of a cartesian coordinate system. Specifically, the position may be indicated by the three coordinates X, Y, and Z.

The expression "orientation" in turn indicates an orientation (for instance, with respect to the position) in the space. It can also be said that the orientation indicates an alignment with direction and/or rotation indication in the three-dimensional space. Specifically, the orientation may be indicated by means of three angles.

The expression "pose" comprises both a position and an orientation. Specifically, the pose may be indicated by means of six coordinates, three position coordinates X, Y, and Z, and three angle coordinates for the orientation.

Advantageous embodiments will be explained, specifically in the following.

In accordance with one embodiment the tracker may be mounted on the robot flange, and the step of moving the robot flange into the at least three poses may comprise the steps of: determining a transformation between the tracker and the external camera in each pose of the at least three poses, and carrying out the hand-eye calibration on the basis of the at least three transformations from the robot base to the robot flange and the at least three transformations from the tracker to the external camera with determination of a transformation between the tracker and the robot flange. A tracker mounted on the robot flange allows a particularly accurate determination of its pose by the external camera, especially if this external camera is configured as a tracking camera.

In accordance with a further embodiment of the calibration method the calibration method may be performed partially iteratively, wherein after the step of carrying out the hand-eye calibration the transformation between the tracker and the robot flange, the transformation between the external camera and the tracker as well as forward kinematics of the robot is applied to determine three new poses of the robot flange and to correspondingly move the robot flange with the tracker (and the robot camera) into these poses. In this manner, the precision and/or accuracy of the hand-eye calibration may, after a first round with an initially coarse calibration, be even further increased by a new round with even better determinable poses.

Preferably, the step of moving the robot camera: may be carried out heuristically and/or systematically on the basis of a first transformation between the robot flange and the robot camera, more particularly on the basis of a stored coarse/estimated transformation or on the basis of a 3D model, more particularly a CAD model; and/or may be carried out on the basis of random movements until the optical calibration pattern or the external camera is detected. In the first case, a first coarse estimation of a transformation may serve the purpose that it is not necessary to search the entire space, but a movement and alignment of the robot camera in the direction of the external camera, if known, is already carried out systematically. Subsequently, the external camera and/or the calibration pattern may be searched in this limited area. This reduces the computing effort and the time required to sense the pose of the external camera. If, however, the calibration method detects a pose of the external camera on the basis of random movements of the robot arm, this may be used in a particularly robust manner and for new environments since data need not be provided in advance.

Specifically, the step of detecting the optical calibration pattern may comprise the steps of: comparing sections of the capturing of the robot camera with a stored calibration pattern, and in the case of sensing conformity of the section with the stored calibration pattern, determining the pose of the calibration pattern by means of image analysis and determining, on the basis of a stored transformation between the pose of the calibration pattern and the pose of the external camera, a pose of the external camera. It is of advantage if the external camera itself need not be sensed directly since it is small, for instance, and a pose cannot be determined so precisely, but indirectly by means of the calibration pattern. The calibration pattern may be designed to be large and be arranged appropriately at the base, for instance, at a height and in an orientation for the robot camera to have a particularly good visibility. If the calibration pattern is a plane calibration pattern, an image analysis for sensing the pose will become particularly simple, in contrast to a direct sensing of the pose of the external camera.

Preferably, the step of detecting a pose of the external camera may comprise the steps of: comparing sections of the capturing of the robot camera, more particularly partial structures of a (three-dimensional) 3D capturing (for instance, by means of a stereo camera) with a stored geometric three-dimensional model, more particularly a CAD model (alternatively or additionally a 2D camera may also be used and the 2D images and/or capturings taken may be compared with the 3D model by using perspective views), of the external camera, and when detecting conformity of the sensed geometric structure with the stored geometric model, determining a pose of the external camera by correlating the 3D structures. In this configuration of the calibration method the external camera is directly sensed by the (capturing of the) robot camera, and a geometric fitting between the sensed external camera and a geometric model is carried out. On the basis of this adaption of the stored model (scaling, rotating, shifting, and others) to the sensed model it is possible to directly determine the pose and the field of view of the external camera.

In accordance with one embodiment the calibration method may further comprise the step of a geometric calibration, more particularly prior to the step of moving the robot camera or after the step of carrying out the hand-eye calibration. Since, in medical engineering, a particularly exact calibration has to be carried out so as to later obtain accuracies of a manipulation of few millimetres, more particularly of less than one millimetre, the geometric calibration is carried out to determine the optical parameters of the camera used and, during a later image analysis, to also correct an optical distortion, a chromatic aberration, or the like. Specifically, the geometric camera calibration may be combined with the hand-eye calibration during the robot movements. Specifically, the calibration pattern is fixed and does not move in space.

Specifically, the geometric calibration may comprise the steps of:

moving the robot camera (in particular systematically or on the basis of heuristics starting out from a coarse position of the calibration pattern relative to the robot camera, or with the aid of random movements); sensing a scene by the robot camera and detecting the calibration pattern with the aid of image processing and object detection. As soon as the calibration pattern has been found, the coarse transformation between the robot camera and the calibration pattern is known. Using this transformation and a known (coarse) transformation between the eye in the hand and the robot flange as well as the forward kinematics, the transformation between the calibration pattern and the robot base is known. Specifically, in a subsequent step for a geometric calibration the pattern may be placed in various positions in the remote and near ranges of the camera and/or the camera may be positioned relatively to the pattern. It must also be placed in various positions so that it appears on every side and corner and in the middle of the capturing of the robot camera (the camera image). Moreover, especially the calibration pattern has to be inclined in relation to the camera. The poses of the robot (and hence of the eye-in-hand camera with respect to the calibration pattern) are calculated with the aid of the known transformations, so that the pattern appears at each of the afore-described positions/positions of the capturing of the robot camera. The robot, more particularly the robot flange with the robot camera, is moved into each of these positions, and the robot camera captures images of the calibration pattern in each of these positions. Finally, the geometric calibration is calculated by means of the images captured. Specifically, a coarsely known transformation between the robot camera and the robot flange may be required, which originates from a CAD model or from a hand-eye calibration.

In accordance with a further embodiment of the calibration method the step of moving the robot flange into at least three different poses may further comprise the step and/or the steps of: determining an area within the field of view of the external camera which can be sensed by the external camera in a particularly exact/precise manner, and moving the robot flange, more particularly the tracker, into this area of the field of view; and/or determining a joint configuration of the robot which enables a particularly exact sensing of the poses, and moving into these poses; and/or moving the robot flange, more particularly the tracker, into at least three poses distributed in the field of view of the external camera, more particularly into those poses in which an angle between the robot flange, more particularly the tracker, and the external camera may be distributed between small and large. The poses into which the robot flange and more particularly the tracker are to be moved are thus chosen and determined such that a particularly high precision of pose sensing is guaranteed. For instance, three poses having only small distances and angle modifications to each other would not provide the required accuracy.

Preferably, the method may comprise the steps of: hand-eye calibration between the robot and the external camera; and/or hand-eye calibration between the robot camera and the external camera; and/or hand-eye calibration between the robot camera and the robot, wherein in the case that all three hand-eye calibrations are carried out and hence redundant transformations exist, error minimization is performed, in particular by means of a mean value estimation. In other words, in particular the calibrations and their variants may thus be combined to minimize an error (in particular with the aid of minimizing methods). This means any combination of the following steps: carrying out a hand-eye calibration between the robot and the external camera (eye-on-base); and/or carrying out a hand-eye calibration between the external camera (eye-on-base) and the robot camera (eye-in-hand); and/or carrying out a hand-eye calibration between the robot camera (eye-in-hand) and the robot. Specifically, after the collecting of the samples the calibrations are calculated and the error is minimized by optimising the calculation of the resulting transformations, so that the error is minimal. The combined calibration steps may particularly also be carried out sequentially. Preferably, one or several hand-eye calibrations may be carried out simultaneously, especially with one or several geometric calibrations. In this case, the camera(s) to be calibrated geometrically take capturings (images) of the calibration pattern for each of the robot poses performed and/or poses of the robot flange, while the transformations of calibrated systems or of systems which need not be calibrated (for instance, a tracking camera or the robot with precise kinematics) are collected. The geometric calibration steps and the hand-eye calibration steps may subsequently be solved sequentially or in parallel.

Specifically, the robot flange and/or the tracker mounted on the robot flange may be used to carry out a calibration of the robot itself. Sensing may take place by means of the external camera as a tracking camera. An actual pose of the tracker is compared with a desired pose of the tracker, and in the case of a deviation a correction value is used for an adaption to the desired pose. The methods of the calibration method may thus particularly also be used for calibrating the robot in that simultaneously the robot poses are sensed while the calibration between the robot camera and the external camera is carried out. The robot kinematics is then calibrated by means of the tracking data and the robot kinematics model is optimised such that it fits to the collected tracking data from the tracker of the robot flange relative to the external camera and/or from the robot camera relative to the calibration pattern. Preferably, in analogy, a tracking camera may be calibrated alternatively or additionally to the robot.

Specifically, the calibration method may comprise the steps of: arranging a static external camera, arranging a camera on the robot as a robot camera, in particular in the field of view of the external camera.

With respect to a surgical navigated assistance system the objects are solved in that it comprises: at least one robot comprising a movable robot arm with a robot flange, which is connected to a robot base, and more particularly a tracker on the robot flange; a robot camera (eye-in-hand) connected to the robot flange and movable by means of the robot arm; and an external camera system comprising at least one external camera, wherein the robot flange, more particularly the tracker, and preferably the robot camera, is movable into a field of view of the external camera. In contrast to the state of the art, the assistance system further comprises a control unit provided and specifically adapted:

- to move the robot camera by means of the controllable robot arm and to take and process a capturing by the robot camera;
- to detect, in the capturing taken, an optical calibration pattern having a predefined transformation/relation to the external camera and/or to determine a pose of the external camera on the basis of the capturing;
- to determine, on the basis of the ascertained pose of the external camera, a transformation between the robot camera and the external camera as well as a field of view of the external camera;
- to move/to control the robot flange, more particularly the tracker, into at least three different poses in the field of view of the external camera and to sense, by means of the external camera, the at least three poses of the robot flange, more particularly the tracker, and to simultaneously sense a transformation between the robot base and the robot flange in each of the at least three poses; and
- to carry out, on the basis of the at least three sensed poses and the at least three sensed transformations, a hand-eye calibration, with determination of a transformation between the robot flange and the robot camera (eye-in-hand), in particular with a transformation between the tracker and the robot camera, and a transformation between the robot flange, more particularly the tracker, and the external camera (eye-on-base) and/or a transformation between the robot flange and the tracker.

In accordance with one embodiment the external camera may be fastened on a base, wherein additionally an optical calibration pattern is arranged at the base in a rigid manner relative to the external camera, and a transformation between a pose of the optical calibration pattern and the pose of the external camera is stored in a storage unit and is provided to the control unit for carrying out a calibration. The control unit senses the pose of the optical calibration pattern by means of the capturing of the robot camera in connection with an image analysis and calculates and determines finally the pose of the external camera and its field of view on the basis of this sensed pose and the known and stored transformation and/or transformation matrix between the pose of the calibration pattern and the external camera.

Preferably, the externally camera may be a stereo camera for tracking, more particularly an infrared-based stereo camera. The tracker may particularly be an infrared-based tracker with a plurality of, more particularly four, infrared markers spaced apart from each other. In this manner a tracker can particularly well be sensed spatially.

Specifically, the robot flange, the tracker, and the robot camera may have approximately a same distance from each other. Thus, these three components are arranged closely adjacent, but at the same distance from each other, and by means of image analysis the control unit may carry out an additional examination of the poses.

In accordance with one embodiment the scene may be set such that the tracker on the robot flange is first of all within the field of view of the external camera. In this manner, calibration is further supported.

Specifically, the calibration method may carry out automatic hand-eye calibration without previous knowledge of the position of the robot camera relative to the flange. Specifically, while the tracker on the robot flange is within the field of view of the external camera, the robot may move the tracker into random poses. In each pose a sample is collected for the calibration of the hand-eye system. A sample comprises a transformation from the robot base to the robot flange and a transformation from the external camera to the tracker. As soon as at least three samples have been collected in the poses in which the tracker was sensed by the external camera, a (preliminary) hand-eye calibration may be calculated, for instance, by means of the Tsai-Lenz algorithm. Subsequently, the transformation between the robot base and the robot camera takes place. Specifically, the calibration method may be continued.

Specifically, the calibration pattern used for the geometric calibration may be the same as the optical calibration pattern for sensing the pose of the external camera. In this manner, only one single calibration pattern is required for the entire calibration method and/or the assistance system.

Preferably, the optical calibration pattern may also be displayed on a display. Thus, a device already available in the operation theatre may be used for the calibration, and it is not necessary to print and apply an own calibration pattern. Specifically, when the calibration pattern is output via a display such as, for instance, an OP monitor, it may be a temporally variable, i.e. a dynamic, calibration pattern. For instance, a scaling of the calibration pattern may be variable in time.

Specifically, the robot camera (eye-in-hand camera) may be calibrated and/or registered to the external camera (with the aid of hand-eye calibration algorithms). Here, the transformation between the calibration pattern and the external camera must be constant. The poses of the robot are generated such that the external camera senses the tracker on the flange in every pose (i.e. is in the field of view), and in turn the robot camera sees and senses the calibration pattern in every pose. In every pose a sample is again collected. A sample comprises, more particularly consists of, the transformation between the tracker on the robot flange and the external camera as well as a transformation between the robot camera and the calibration pattern. The carrying out of an appropriately adapted hand-eye calibration provides in this case the transformations between the calibration pattern and the external camera as well as the transformation between the robot camera and the tracker tracked by the external camera.

In accordance with a further embodiment the external camera may be fastened on a base and the optical calibration pattern may be adapted to be arranged relatively moveable to the external camera. The external camera tracks the relatively moveable calibration pattern, in particular by means of a calibration tracker with optical markers which is arranged rigidly on the calibration pattern (for instance, and optical rigid body tracker), wherein in this case a static transformation (for instance, a transformation matrix) from (the pose of) the calibration tracker to (the pose of) the calibration pattern is stored in a storage unit, so that the external camera tracks the pose of the calibration tracker and the pose of the calibration pattern can be determined by means of the static transformation. Also, as an alternative to the calibration tracker, a method of image processing may be used to track the calibration pattern, so that the calibration pattern is sensed directly and a pose is determined. By the tracking of the optical calibration pattern the control unit can, on the basis thereof, calculate a dynamic transformation from the pose of the optical calibration pattern to the pose of the external camera and use same for a calibration.

In accordance with one embodiment the external camera may be an optical camera. In this case, a geometric calibration of the external camera may be carried out. In this case, the robot does not (or not only) move the robot camera but moves a calibration pattern (which is fastened on the robot flange in this case) in front of the external camera (eye-on-base) so as to position it.

Preferably, the robot camera may be a tracking camera.

With respect to a computer-readable storage medium the objects are solved in that it comprises instructions which, when executed by a computer, cause same to perform the method steps of the calibration method in accordance with the present disclosure.

In accordance with a very preferred embodiment the calibration method and a specifically adapted control unit of the assistance system comprise the following steps and/or configurations. Specifically, the external camera/eye-on-base (camera) may be a tracking camera and the robot camera eye-in-hand (camera) may be an optical 2D or 3D camera, wherein a tracker is mounted rigidly on the robot flange and hence also on the robot camera. In a first step, a coarse positioning of the robot in the field of view of the external camera (eye-on-base camera) takes place. The robot moves the robot camera/eye-in-hand in space (for instance, systematically or on the basis of heuristics which assumes a coarse position of the external camera/eye-on-base relative to the robot camera/eye-in-hand, or with the aid of random movements). Here, a coarsely known transformation between the eye in the hand and the robot flange is required or at least helpful. It may, for instance, originate from a CAD model. The robot camera senses the scene and tries to find the external camera by either: searching a tracker or a known pattern (calibration pattern) mounted in the area of the external camera, or finding it directly by image processing and identifying the external camera in the capturing (in the image) if it was sensed. The position, more particularly the pose, of the external camera is determined (more particularly estimated) by: By means of the position of the pattern (calibration pattern) and/or the tracker relative to the external camera (must be known, but may be very coarse), or by adapting a camera model to the identified camera and determining the coarse position of the external camera. By means of these steps a (at least coarse) transformation between the external camera and the robot camera is known. In order to continue, a coarse transformation between the robot camera and the robot flange is helpful. It might, for instance, originate from a CAD model. By means of this transformation and the coarse transformation between the robot camera (eye-in-hand) and the external camera (eye-on-base) in combination with a known field of view of the external camera, any information is available for moving the robot camera actuated by the robot into the field of view of the external camera. Subsequently, the step of solving the problem of the hand-eye calibration follows in particular. For this step, the tracker on the robot flange has to be disposed close to the robot flange itself, so that it may be assumed that it is also disposed in the field of view of the eye-on-base camera during a movement of the robot. Alternatively, a coarse position of the tracker relative to the robot flange may also be known (for instance, from a CAD model). For a hand-eye calibration the tracker fastened on the robot flange is (along with the robot) moved in the field of view of the external camera. The field of view of the external camera is known. This information is used to calculate the poses for the robot and hence the poses for the tracker. The poses of the tracker relative to the external camera are generated such that an error of the hand-eye calibration is minimized. For calculating the poses the following information may be taken into account: Most accurate area within the field of view of the external camera; and/or joint configuration of the robot with which the best accuracy is to be expected; and/or distribution of the poses of the tracker within the field of view of the external camera (eye-on-base); and/or distribution of the poses of the tracker within the field of view of the external camera, so that the angles between the tracker and the camera may be distributed between large and small. The robot is controlled and/or moved to the calculated poses, and samples are collected both for the transformation between the robot flange and the robot base as well as for the transformation between the external camera and the tracker on the robot flange. Finally, hand-eye calibration is calculated with the aid of known methods, in particular with the Tsai-Lenz algorithm. In accordance with an optional step an intermediate calibration of the hand-eye calibration may be calculated with known methods, such as the Tsai-Lenz algorithm, after the sensing of at least three poses. This new hand-eye calibration comprises a transformation between the tracker and the robot flange. Using the transformation from the external camera to the tracker, from the tracker to the flange and forward kinematics of the robot, the poses between the external camera and the robot base may be updated with a more exact transformation. In order to collect further random samples for an even more exact hand-eye calibration, the calculated poses are newly calculated with the new transformation, or new poses for the robot are calculated with the afore-described approach. The robot then continues with the movement of the tracker and further samples are collected.

Any disclosure in connection with the surgical navigated assistance system of the present disclosure also applies for the calibration method of the present disclosure and vice versa.

BRIEF DESCRIPTION OF THE DRAWINGS

The present disclosure will be explained in detail in the following by means of preferred embodiments with reference to the accompanying Figures.

The Figures are of schematic nature and shall only serve the understanding of the present disclosure. Equal elements are provided with the same reference signs. The features of the various embodiments are interchangeable.

DETAILED DESCRIPTION

Figure 1:
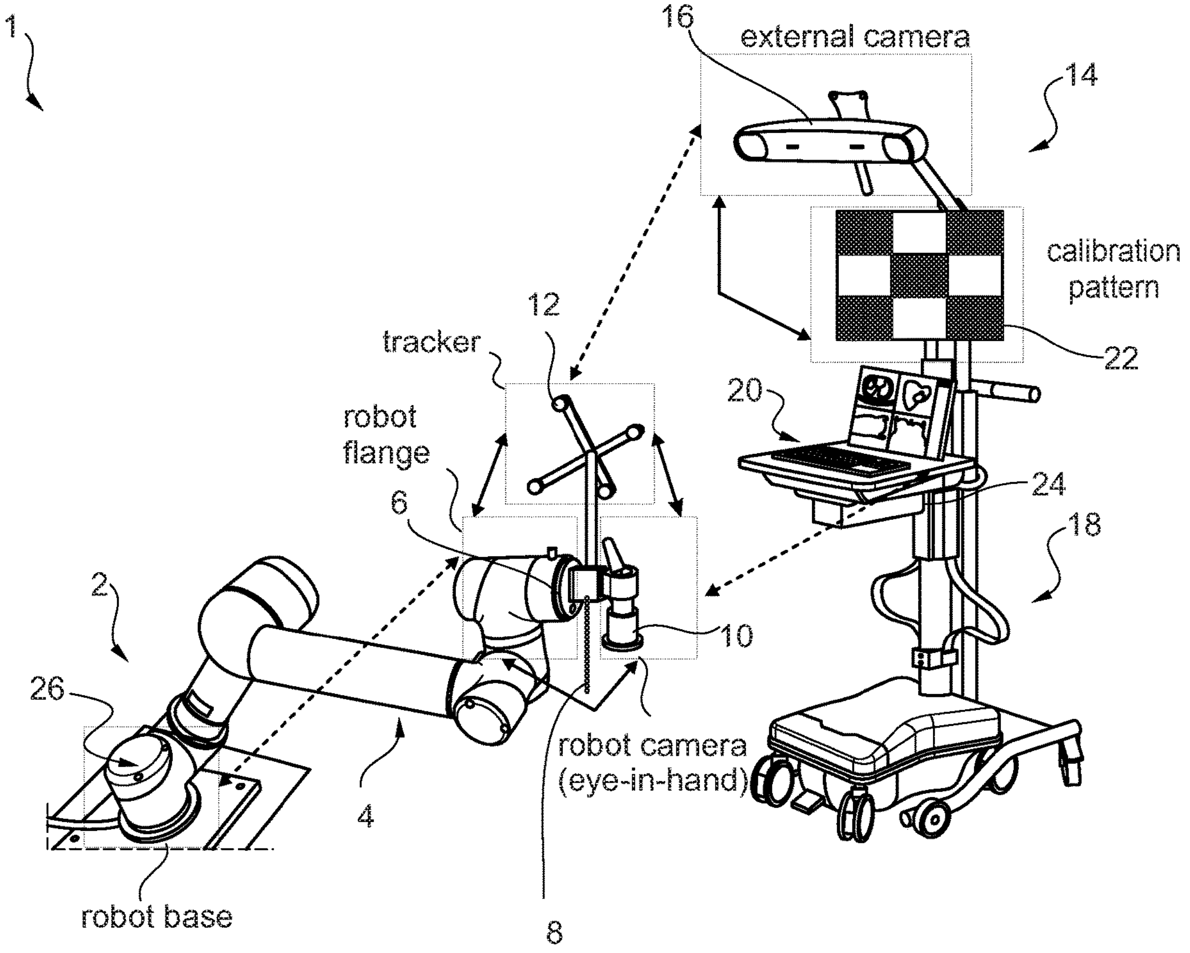
FIG. 1 is a schematic perspective view of a surgical assistance system of a preferred embodiment in which a calibration method according to a preferred embodiment is used for automatic calibration.

FIG. 1 shows a surgical assistance system 1 in accordance with a first preferred embodiment, which carries out an automated calibration, presently a calibration method in accordance with a first preferred embodiment.

The surgical assistance system 1 has a robot 2 with a controllable and movable robot arm 4 which comprises an end portion with a robot flange 6. An end effector 8, for instance, in the form of grasping forceps or, as in the instant case, a rod is mounted on this robot flange 6 so as to manipulate an object with the end effector 8. For sensing the object and for a corresponding control of the robot, a camera 10 on the robot 2 (eye-in-hand; in the following called robot camera) is mounted on the robot flange 6, the field of view of which points in the direction of the end effector 8, for serving as an eye of the robot 2 and for optically sensing in particular a portion of the end effector 8. In this manner, objects may be sensed and, after the calibration of robot camera 10 to robot 2, also be controlled and manipulated appropriately. Like the end effector 8, the robot camera 10 may also be controlled and moved. Moreover, a tracker 12 in the form of a geometric tracker with four marking points spaced apart from each other is provided on the robot flange 6 so as to sense the tracker 12 and hence the robot flange 6, by means of an external camera system 14 with an external camera 16, in a particularly precise manner spatially with respect to a pose, i.e. a position and an orientation.

The external camera 16 on a static base 18 is directed to the robot 2 and senses, when the robot arm 4 with the tracker 12 and the robot camera 10 is moved in correspondence with its kinematics into the field of view of the external camera 16, the robot flange 6, the tracker 12, and the robot camera 10.

The surgical assistance system 1 comprises, for a function and/or configuration of an automated calibration, furthermore a control unit 20 which is specifically adapted to carry out an automatic calibration between the robot camera 10, the external camera 16, and the robot 2.

In contrast to the state of the art, not only a camera is thus provided, be it a camera on the robot or an external camera, but specifically two cameras 10, 16 are provided, namely a controllable and actively guidable robot camera 10 on the robot 2 itself and an external camera 16 which is statically fastened on the base 18 and does not move along with the robot 2.

A plane face with an imprinted optical calibration pattern 22 in the form of a chequered pattern is fastened on the base 18 below the external camera and has a defined pose relative to the external camera 16. Alternatively, the optical calibration pattern may also be displayed by means of a monitor. Specifically, the chequered pattern comprises individual quadrangles with further markings. This optical calibration pattern 22 serves for a particularly easy detection of a pose.

The control unit 20 is specifically adapted to move, in a first step, more particularly after a coarse positioning of the robot 2 in a field of view of the external camera 16 (eye-on-base (camera)), the robot camera 10 fastened on the robot flange 6 randomly in space by means of random movements. In this process, the robot camera 10 continuously senses the environment and/or takes a continuous (video) capturing A and provides same in a computer-readable manner to the control unit 20. The control unit 20 in turn analyses this capturing A so as to detect the external camera 16 and the pose thereof.

Concretely, the control unit 20 is adapted to detect, in the capturing A of the robot camera 10, the optical calibration pattern 22 which is also stored in a storage unit 24 and provided to the control unit 20. The optical calibration pattern 22 is particularly easy to detect since it may be arranged in any, but predefined, relation to the external camera 16. For instance, the optical calibration pattern may be arranged above 1.5 m, so that it is not completely concealed by medical professionals or by waist-high objects. Also, this is a plane face.

On the basis of the optical calibration pattern 22 sensed by the robot camera 10, the control unit 20 then determines a pose of this optical calibration pattern 22. Since the calibration pattern 22 is, depending on an angle of a normal of the plane surface to a direct connection line between the robot camera 10, represented in a distorted, but recalculable manner in the capturing A, a pose, i.e. a position and an orientation, may be determined by means of common methods of image analysis.

In the storage unit 24, apart from the optical calibration pattern 22 also a transformation, here a transformation matrix, between the pose of the calibration pattern 22 and the pose of the external camera 16 is stored. It may also be said that a transformation matrix between a local coordinate system (COS) of the calibration pattern 22 and the local COS of the external camera 16 is stored. The control unit 20 now determines on the basis of the sensed pose of the calibration pattern 22 in combination with the stored transformation the pose of the external camera and can thus calculate a (coarse) transformation between the external camera 16 and the robot camera 10, which may even be further specified. The individual local coordinate systems and/or groups are illustrated as dashed boxes in FIG. 1 for better understanding of the present disclosure.

In other words, a transformation between the eye-on-base camera and the eye-in-hand camera as well as a field of view of the external camera 16 is thus known. In order to continue with the calibration, a coarse transformation between the robot camera 10 (eye-in-hand camera) and the robot flange 6 is helpful. In the storage unit 24, a coarse 3D model (CAD model) is stored for this purpose, from which the control unit 20 determines a first coarse estimation of such a transformation.

On the basis of the determined transformation between the external camera 16 and the robot camera 10 as well as optionally the first coarse transformation between the robot flange 6 and the robot camera 10 as well as a known field of view of the external camera 16, all necessary data are available for moving the robot camera 10 in the field of view of the external camera 16 and for carrying out a calibration.

In other words, with the transformation between the eye-in-hand camera and the eye-on-base camera in combination with a known field of view of the eye-on-base camera it is possible to move the eye-in-hand camera robot-like in the field of view of the eye-on-base camera. Thus, so to speak, an optical framework for the movement of the robot camera 10 within this predefined optical framework is defined.

In a next step, the solution of the problem of the hand-eye-calibration takes place. For this step, the tracker 12 is disposed close to the robot flange 6 of the robot 2, so that it may be assumed that it is disposed preferably next to the robot camera 10 and preferably the robot flange 6, also in the field of view of the robot camera 10. Alternatively, a coarse pose of the tracker 12 relative to the robot flange 6 may also be known, in particular from a CAD model stored in the storage unit 24.

For a hand-eye calibration the tracker 12 fastened on the robot flange 6 of the robot 2 is, by means of the control unit 20, moved along with the robot arm 4 in the known field of view of the external camera 16.

Data are used to calculate the poses for the robot 2 and hence for the tracker 12. The poses of the tracker 12 relative to the external camera 12 are generated such that a hand-eye calibration error is minimized. For calculation of the poses especially the following data are taken into account: a most accurate area within the field of view of the external camera 16; such a joint configuration of the robot 2 with which the best accuracy is to be expected; a distribution of the poses of the tracker 12 within the entire field of view of the external camera so as to sense as different poses as possible; and/or distribution of the poses of the tracker 12 within the field of view of the external camera 16, so that angles between the tracker 12 and the camera 16 between large and small may be selected and controlled differently. The control unit 20 determines at least three poses for the robot flange 6 with the tracker 12.

Subsequently, the control unit 20 controls the robot 2 such that it is moved into the calculated poses. In this process, data (samples) both for a transformation between the robot flange 6 and a robot base 26 and for a transformation between the external camera 16 and the tracker 12 on the flange are collected.

Preferably, in an optional step after the sensing of at least three poses, an intermediate calibration of the hand-eye calibration may be calculated with known methods, more particularly the Tsai-Lenz algorithm. The new hand-eye calibration comprises a transformation between the tracker 12 and the robot flange 6. Using the transformation from the external camera 16 to the tracker 12, from the tracker 12 to the robot flange 6 and forward kinematics of the robot 2, the known transformation and/or pose between the external camera 16 and the robot base 26 may be updated with a more exact transformation. In order to collect further (random) samples for an even more exact hand-eye calibration, the afore-calculated poses are newly calculated with the new transformation now. Alternatively or additionally, also new poses for the robot 2 may be calculated with the foregoing approach. The robot 2 then continues with the movement of the tracker 12, and appropriate random samples are collected.

Finally, the control unit 20 then calculates the hand-eye calibration by means of known methods, more particularly the Tsai-Lenz algorithm, on the basis of the samples sensed. The control unit 20 calculates in particular the transformation between the robot camera 10 and the robot flange 6 and provides a calibration and/or registration between the robot camera 10 and the robot 2 as well as a calibration between the external camera 16 and/or the tracker and the robot flange 6 and hence the robot 2. Thus, the problem of hand-eye calibration has been solved.

In FIG. 1, all relevant system names and transformations between the robot 2 and the two cameras 10, 16 are illustrated. The continuous arrows represent transformations that may be calculated from the hand-eye calibration. The dashed arrows stand for transformations that may be measured and more particularly be calibrated, preferably by means of a geometric calibration.

In addition to the afore-described configuration the robot camera 10, as an optional calibration, is also calibrated geometrically. This geometric calibration may be carried out optionally by the control unit 20. This geometric calibration is only necessary if the robot camera 10 and/or the external camera also are to be calibrated geometrically. The geometric calibration is independent of the foregoing hand-eye calibration.

For this step, a camera calibration algorithm is used. For the geometric camera calibration, again a calibration pattern is required. This calibration pattern may especially be the optical calibration pattern 22. For the geometric calibration, the calibration pattern has to be place in the field of view of the camera, and calibration takes placed with the aid of the known geometry of the calibration pattern and a corresponding calibration algorithm so as to calculate (optical) camera parameters such as focal length and distortion coefficients from the distortions sensed. It is crucial that the calibration pattern is moved relative to the camera, either by displacing of the calibration pattern or by moving of the camera.

In contrast to the state of the art, however, in the present disclosure the geometric camera calibration is combined with the hand-eye calibration during the movement of the robot. In this scenario the calibration pattern is fixed on the base.

The control unit 20 is adapted to carry out the following partial steps. In a first step, the robot camera 10 is again moved by means of the robot arm 4, for instance, systematically, on the basis of heuristics starting out from a coarse position of the calibration pattern relative to the robot camera (by means of a known coarse transformation between the robot camera 10 and the robot flange 6), or again with the aid of random movements.

The robot camera 10 again senses the environment and is adapted to detect the calibration pattern 22 with the aid of image processing and object detection. Once the (geometric) calibration pattern 22 has been detected, the coarse transformation between the robot camera 10 and the (geometric) calibration pattern 22 is known. Using this transformation and a known (coarse) transformation between the robot camera 10 and the robot flange 6 as well as forward kinematics, the transformation between the calibration pattern 22 and the robot base 26 can be determined by the control unit 20.

The control unit 20 is adapted to place, in a subsequent step, the calibration pattern 22 for calibration in various positions in the remote and close areas of the robot camera 10. Moreover, the control unit 20 is adapted to also place the calibration pattern 22 in various positions, so that it appears on every side and in every corner as well as in the middle of the camera image of the robot camera 10. Moreover, the control unit 20 is adapted to incline the calibration pattern 22 in relation to the robot camera 10. In a traditional approach these steps have to be performed manually. In accordance with the present disclosure the poses of the robot 2 (and hence of the robot camera 10 with respect to the calibration pattern 22) are calculated with the aid of the known transformations, so that the calibration pattern 22 appears at any of the afore-described positions of the capturing A taken by the robot 10 and may be processed appropriately by the control unit 20 so as to carry out the geometric calibration. The robot is, controlled by the control unit 20, moved into each of these positions, and the robot camera 10 takes capturings A (images) of the calibration pattern 22 in each of these positions. Subsequently, the control unit 20 calculates the geometric calibration of the robot camera 10 by means of the images taken.

Figure 2:
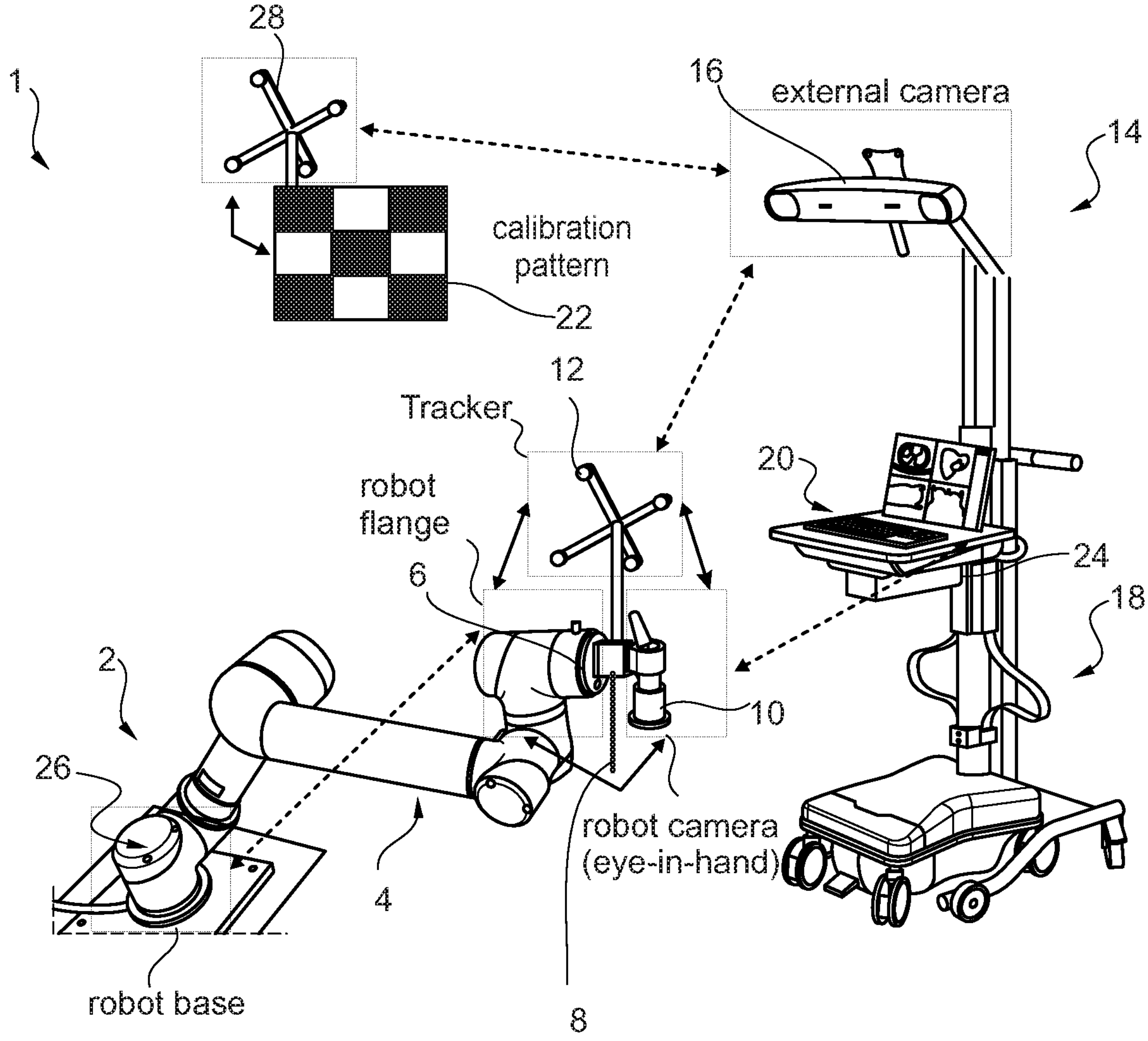
FIG. 2 is a schematic perspective view of a surgical assistance system in accordance with a further preferred embodiment with a movable calibration pattern, in which a calibration method according to a preferred embodiment is used for automatic calibration.

FIG. 2 shows a schematic perspective view of a surgical assistance system 1 in accordance with a further preferred embodiment. In contrast to the embodiment of FIG. 1, the surgical assistance system 1 of this embodiment comprises a calibration pattern 22 which is relatively movable to the external camera 16, which may be arranged at different positions in space, for instance, held manually, or by means of an arm which can, for instance, be actuated actively. The relatively movable calibration pattern 22 is arranged in the field of view of the external camera 16, and the external camera 16 senses a pose of the calibration pattern 22 to the external camera 16 by means of a calibration tracker 28 with optical markers which is fixed to the calibration pattern 22, wherein the control unit 20 is provided with the static transformation from the calibration tracker 28 to the calibration pattern 22, is, for instance, stored in a storage unit as a numerical matrix. By the fact that the calibration pattern 22 in this embodiment is not mounted rigidly, but is relatively movable, it may, during an operation, be arranged at favourable places in the operation theatre, where the calibration pattern 22 does not disturb, or where it offers a particularly good position for an accurate calibration. The external camera 16 thus senses a (dynamic) pose of the calibration pattern 22 and provides a (dynamic) transformation, for instance, as a transformation matrix, for a calibration. So, if the calibration pattern 22 is sensed, the pose of the external camera 16 and a transformation between the robot camera 10 and the external camera 16 may also be determined by means of the dynamic transformation determined.

Figure 3:
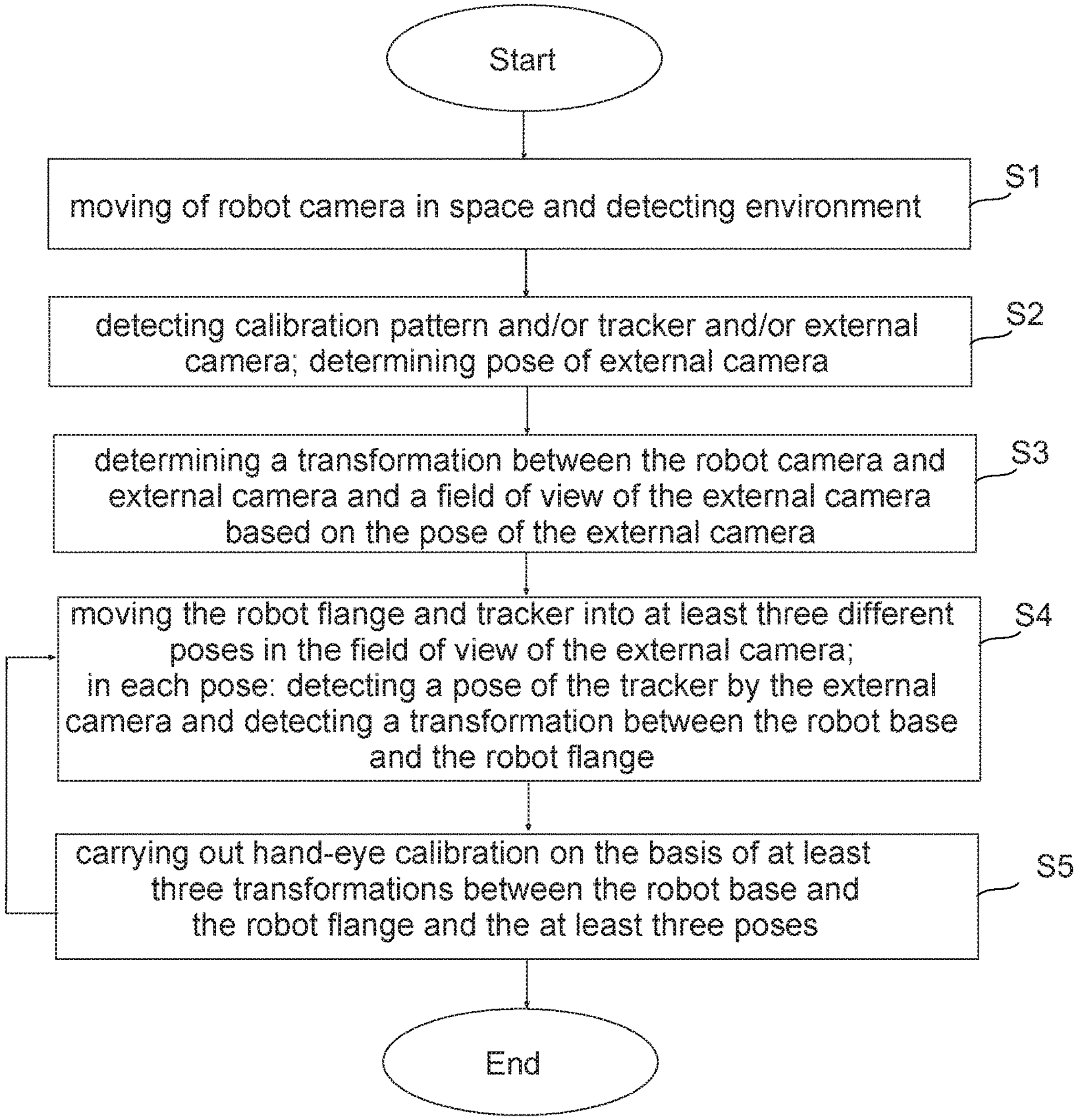
FIG. 3 is a flowchart of a calibration method in accordance with a further preferred embodiment.

FIG. 3 shows, in the form of a flowchart, a course of procedure of a calibration method in accordance with a preferred embodiment. It may especially be used in a surgical navigated assistance system of FIG. 1.

In a first step S1, a robot camera as a camera connected to a robot arm and adapted to be moved by it (eye-in-hand) is moved in space, and a continuous capturing is taken by the camera and a scene and/or environment is sensed.

In a step S2, a predefined optical calibration pattern and/or an external tracker and the pose thereof is detected with a predefined transformation to a pose of the external camera and/or a pose of the external camera on the basis of the capturing.

In a step S3, on the basis of the ascertained pose of the external camera, a transformation between the robot camera and the external camera and a field of view of the external camera is determined.

In a step S4, the robot flange with a tracker mounted on the robot flange is moved into at least three different poses in the field of view of the external camera, and the at least three poses of the tracker are sensed by the external camera, and simultaneously a transformation between the robot base and the robot flange is sensed.

Finally, in step S5, a hand-eye calibration with determination of a transformation to the external camera takes place on the basis of the at least three sensed poses and the at least three transformations between the robot base and the robot flange.

LIST OF REFERENCE SIGNS

1 surgical assistance system
2 robot
4 robot arm
6 robot flange
8 end effector
10 robot camera
12 tracker
14 external camera system
16 external camera
18 base
20 control unit
22 calibration pattern
24 storage unit
26 robot base
28 calibration tracker
A capturing robot camera
S1 Step moving of robot camera
S2 Step detecting of pose of external camera
S3 Step determining of transformation and field of view of external camera
S4 Step moving of tracker on the robot flange into several poses in the field of view
S5 Step carrying out of hand-eye calibration

The invention claimed is:

1. A calibration method for an automated calibration of a robot camera in relation to a medical robot, the robot camera being movably guided on a robot flange of a robot arm, which is connected to a robot base, and for an automated calibration of an external camera system, which has at least one external camera, in relation to the medical robot, comprising:

moving the robot camera by the robot arm during sensing and capturing by the robot camera;

detecting, based on the capturing, a pose of at least one of an optical calibration pattern that is predefined or of an external tracker, each having a predefined transformation from this detected pose to a pose of the external camera, and/or detecting, based on the capturing, a pose of the external camera;

determining, based on the pose of the external camera, a transformation between the robot camera and the external camera, and determining a field of view of the external camera;

moving the robot flange into at least three different poses in the field of view of the external camera, and sensing the at least three poses of the robot flange via the external camera, and simultaneously sensing a transformation between the robot base and the robot flange; and carrying out, on the basis of the at least three sensed poses and the at least three sensed transformations, a hand-eye calibration, with determination of at least one of a transformation from the robot flange to the robot camera, a transformation from the external camera to the robot base, or a transformation between the robot flange and the tracker.

2. The calibration method according to claim 1, wherein, with a tracker fastened on the robot flange, moving the robot flange into the at least three poses comprises:

determining a transformation between the tracker and the external camera in each pose of the at least three poses; and carrying out the hand-eye calibration based on the at least three sensed transformations from the robot base to the robot flange and the at least three sensed transformations from the tracker to the external camera with determination of a transformation between the tracker and the robot flange.

3. The calibration method according to claim 2, wherein moving the robot flange and carrying out the hand-eye calibration of the calibration method are carried out iteratively, and after a first round of carrying out the hand-eye calibration, the transformation between the tracker and the robot flange, the transformation between the external camera and the tracker, as well as forward kinematics of the robot are used to determine new poses of the robot flange and to move the robot flange correspondingly into these poses for a next iteration.

4. The calibration method according to claim 1, wherein moving the robot camera is at least one of:

carried out at least one of heuristically or systematically on the basis of a first transformation between the robot flange and the robot camera on the basis of a stored first transformation on the basis of a 3D CAD model; or carried out on the basis of random movements until the optical calibration pattern or the external tracker or the external camera is detected.

5. The calibration method according to claim 1, wherein detecting the optical calibration pattern comprises:

comparing sections of the capturing of the robot camera with a stored calibration pattern and when there is conformity determining the pose of the calibration pattern via image analysis and determining, on the basis of a stored transformation between the pose of the calibration pattern and the pose of the external camera, a pose of the external camera.

6. The calibration method according to claim 1, wherein detecting a pose of the external camera comprises:

comparing sections of the capturing of the robot camera with a stored geometric model of the external camera, and when detecting conformity with the stored geometric model, determining a pose of the external camera by correlating three-dimensional structures.

7. The calibration method according to claim 1, wherein the calibration method further comprises performing a geometric calibration prior to moving the robot camera or after carrying out the hand-eye calibration.

8. The calibration method according to claim 1, wherein moving the robot flange into at least three different poses further comprises at least one of:

determining an area within the field of view of the external camera which can be sensed in a particularly accurate manner and moving the tracker, into this area of the field of view;

determining a joint configuration of the robot which allows a particularly accurate sensing of the poses, and moving into same;

moving the tracker into at least three poses distributed in the field of view of the external camera, including those poses where an angle between the tracker and the external camera may be distributed between small and large.

9. The calibration method according to claim 1, further comprising at least one of:

providing hand-eye calibration between the robot and the external camera;

hand-eye calibration between the robot camera and the external camera; or at least one of providing hand-eye calibration between the robot camera and the robot or determining a transformation between the tracker and the robot flange via a hand-eye calibration, wherein when all three hand-eye calibrations are carried out and hence redundant transformations exist, error minimization is carried out.

10. A surgical navigated assistance system, comprising:

at least one robot comprising a robot arm with a robot flange connected to a robot base, the robot arm being movable;

a robot camera connected to the robot flange and movable via the robot arm; and an external camera system comprising at least one external camera, at least one of the robot flange or the robot camera being movable into a field of view of the external camera, the surgical navigated assistance system comprising a control unit adapted:

to move the robot camera via the robot arm and to take and process a capturing by the robot camera;

to sense, in the capturing, a pose of at least one of an optical calibration pattern or an external tracker, each having a predefined transformation to the external camera, and/or to determine a pose of the external camera based on the capturing;

to determine, based on the pose of the external camera, a transformation between the robot camera and the external camera as well as a field of view of the external camera;

to move the robot flange into at least three different poses in the field of view and to sense, via the external camera, the at least three different poses and to simultaneously sense at least three transformations between the robot base and the robot flange; and to carry out, based on the at least three different poses and the at least three transformations, a hand-eye calibration.

11. The surgical assistance system according to claim 10, wherein:

the external camera is fastened on a base and additionally the optical calibration pattern is arranged at the base in a rigid manner relative to the external camera, and a static transformation between a pose of the optical calibration pattern and the pose of the external camera is provided to the control unit for the determination of the pose of the external camera, or the external camera is fastened on a base and the optical calibration pattern is relatively movable to the external camera which tracks the optical calibration pattern and a static transformation to the optical calibration pattern, wherein, based thereon, the control unit calculates a dynamic transformation from the pose of the optical calibration pattern to the pose of the external camera.

12. The surgical assistance system according to claim 10, wherein the external camera is a stereo camera for tracking, and the tracker on the robot flange is an infrared-based tracker with a plurality of infrared markers spaced apart from each other.

13. The surgical assistance system according to claim 10, wherein the robot flange, the tracker, and the robot camera are rigid with respect to each other.

14. A non-transitory computer-readable storage medium comprising instructions which, when executed by a computer, cause the computer to perform the calibration method according to claim 1.

15. The surgical navigated assistance system according to claim 10, wherein the external camera tracks the optical calibration pattern via a calibration tracker with optical markers which is mounted rigidly on the calibration pattern.

* * * * *